United States Patent [19]

Goldberg

[11] 4,377,516

[45] Mar. 22, 1983

[54] ANTIGENIC LINEAR PEPTIDE COMPOUNDS

[75] Inventor: Erwin Goldberg, Evanston, Ill.

[73] Assignee: Northwestern University, Evanston, Ill.

[21] Appl. No.: 329,242

[22] Filed: Dec. 10, 1981

[51] Int. Cl.³ .......................................... C07C 103/52
[52] U.S. Cl. ............................................. 260/112.5 R
[58] Field of Search ................................. 260/112.5 R

[56] References Cited

U.S. PATENT DOCUMENTS 4,310,456 1/1982 Goldberg ..................... 260/112.5 R Primary Examiner—Delbert R. Phillips

[57] ABSTRACT

The novel antigenic linear peptide compounds of this invention comprise sequences of from 10 to 14 amino acids which include the sequence arginine-methionine-valine-serine-glycine-glutamine-threonine-arginine-leucine-aspartic acid, all of the amino acids with the exception of glycine being in their L-forms. The compounds have utility in vaccines for reducing fertility of mammals.

6 Claims, No Drawings

ANTIGENIC LINEAR PEPTIDE COMPOUNDS

RELATED APPLICATION

This application is related to the subject matter of copending application Ser. No. 179,049, filed Aug. 18, 1980, which discloses the nine amino acid sequence compound: arginine-methionine-valine-serine-glycine-glutamine-threonine-arginine-leucine.

BACKGROUND AND PRIOR ART

Mammalian spermatozoa have been known to be antigenic for many years. More recently, it has been demonstrated that mammalian sperm contain an antigenic enzyme, which is known as the $C_4$ isozyme of lactate dehydrogenase (LDH-X, LDH-$C_4$). LDH-$C_4$ has been isolated in pure crystalline form from mouse testes. Goldberg (1972) *J. Biol. Chem.* 247:2044–2048. The enzyme has a molecular weight of 140,000 and is composed of four identical C subunits. The amino acid sequence and three-dimensional structure of LDH-C4 has been studied and partially determined by a number of investigators. See Musick et al (1976) *J. Mol. Biol.* 104:659–668; and Wheat et al (1977) *Biochem. & Biophys. Res. Comm.*, 74, No. 3:1066–1077. Wheat et al determined the sequence of the essential thiol peptide from amino acid 159 to 171, and found this to be nearly identical to essential thiol peptides from other vertebrate LDH isozymes.

In 1974, Dr. Erwin Goldberg reviewed the effects of immunization with LDH-X (LDH-$C_4$) on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties, makes the immunological approach to fertility control feasible." Karolinska Symposia on Research Methods in Reproductive Endocrinolgy, 7th Symposia: Immunological Approaches to Fertility Control, Geneva, 1974 202–222. However, such synthetic antigenic peptides remained a goal and not achievement, although their theoretical desirability has been recognized. In 1979, Dr. Erwin Goldberg summarized the state of the art as follows:

"In conclusion, and on a practical basis, immunotherapy for birth control requires more than effectiveness, specificity, reversibility, and absence of systemic side reaction. Rather large amounts of the antigen must be available in unequivocally pure form. This condition probably cannot be met by a natural product enzyme antigen from sperm or testes. Rather, contraceptive technology requires a synthesizable peptide fragment retaining antigencity and provoking a response which impairs fertility. Completion of the structural analysis of LDH-$C_4$ should allow mapping of antigenic determinants and synthesis of such peptides for use in a new contraceptive technology." *"Recent Advances in Reproduction and Regulation of Fertility,"* G. P. Talwar, editor, Elsevier/North Holland Biomedical Press (1979).

SUMMARY OF INVENTION

It has now been discovered that antigenic peptides can be prepared by synthesizing a linear sequence of 10 to 14 amino acids including the sequence: arginine-methionine-valine-serine-glycine-glutamine-threonine-arginine-leucine-aspartic acid. All of the amino acids used to prepare these peptide compounds are in their L-form with the exception of glycine. The arginine is at the N-terminal and aspartic acid is at the C-terminal, or in the C-terminal end portion. Although not known with certainty, it is believed that the foregoing sequence of ten amino acids corresponds to amino acids 101 to 111 of LDH-$C_4$. This is contrary to a recently published tentative sequence. Musick et al (1979) *J. Biol. Chem.*, 254, No. 16:7621–7623. The other compounds respectively are believed to correspond to the 101–112, 101–113, 101–114, and 101–115 sequence of LDH-$C_4$, contrary to Musick et al. In the sequence numbering convention used, there is no amino acid 104.

DESCRIPTION OF INVENTION

The present invention relates to novel antigenic linear peptides having chain length from 10 to 14 amino acids. These peptides all include the N-terminal sequence:

N-Arg-Met-Val-Ser-Gly-Gln-Thr-Arg-Leu-Asp.

More specifically the invention generically comprises the following five peptide compounds.

(P-1)  N-Arg-Met-Val-Ser-Gly-Gln-Thr-Arg-Leu-Asp-C, (P-2)  N-Arg-Met-Val-Ser-Gly-Gln-Thr-Arg-Leu-Asp-Leu-C, (P-3)  N-Arg-Met-Val-Ser-Gly-Gln-Thr-Arg-Leu-Asp-Leu-Leu-C, (P-4)  N-Arg-Met-Val-Ser-Gly-Cln-Thr-Arg-Leu-Asp-Leu-Leu-Gln-C, and (P-5)  N-Arg-Met-Val-Ser-Gly-Gln-Thr-Arg-Leu-Asp-Leu-Leu-Gln-Arg-C, wherein the letter "N" designates the N-terminal amino acids, while the letter "C" designates the C-terminal amino acids. Gly represents glycine, and Arg, Met, Val, Ser, Gln, Thr, Leu, and Asp respectively represent the L-amino acid forms arginine, methionine, valine, serine, glutamine, threonine, leucine, and aspartic acid.

The peptide compounds of the present invention P-1, P-2, P-3, P-4, and P-5 can be synthesized from their constituent amino acids. For example, the synthesis can be carried out by the Merrifield solid phase method, as described in *J.A.C.S.* 85:2149–2154 (1963). This solid phase method for synthesizing sequences of amino acids is also described in Stewart and Young, *Solid Phase Peptide Synthesis* (W. H. Freeman and Co., San Franncisco, 1969), pages 1–4. In this procedure, the C-terminal amino acid, such as aspartic acid for the P-1 compound of this invention is attached to chloromethylated polystyrenedivinylbenzene copolymer beads. Each subsequent amino acid, with suitable protecting group, is then added sequentially to the growing chain. For example, as described in the Merrifield article, the protective group may be a carbobenzoxy group. By the procedure of coupling, deprotection, and coupling of the next amino acid, the desired amino acid sequence and chain length can be produced. As a final step, the protective group is removed from the N-terminal amino acid such as from the N-terminal arginine, and then is cleaved from the resin, using a suitable reagent, such as trifluoroacetic acid and hydrogen bromide. Since this synthesis procedure is well known, it is not believed that it will be necessary to further describe it herein. The peptide of this invention can be prepared by this synthesis procedure for use in reducing the fertility of mammals.

To utilize the antigenic peptides of this invention (P-1 to P-5) in the form of fertility reducing vaccines, the peptide used is conjugated to a carrier molecule, which is preferably a protein which itself elicits an antigenic response and which can be safely administered. For example, the selected peptide can be coupled to tetanus toxoid for administration by intramuscular injection. For example, a mixture of 1μ Mole tetanus toxoid, 60μ Mole antigenic peptide, and 18 millimoles 1-ethyl-3-(3 dimethyl aminopropyl) carbodiimide hydrochloride reacted in water (pH 6) for 12 hours at room temperature and 24 hours at 4° C. gives a product containing 3.5 moles of peptide/mole of tetanus toxoid. Excess reactants can be removed by dialysis or gel filtration. See Pique et al, *Immunochemistry*, 15:55–60 (1978). Alternatively, the peptide may be coupled using bisdiazotized benzidine (Bassiri et al, *Endocrinology*, 90:722 (1972)) or glutaraldehyde.

For intramuscular injection, the coupled peptide may be suspended in a sterile isotonic saline solution, or other conventional vehicle, and, if desired, an adjuvant may be included. A preferred use of such a vaccine is for administration to human females. Antibodies will be formed, which will appear in the oviduct fluids and thereby achieve a significant reduction in fertility. For this purpose, the amount to be administered will range from about 1 to 10 milligrams (mg) of the antigenic peptide.

The peptide compounds of this invention and their method of preparation are further illustrated by the following examples.

EXAMPLE I

Preparation of Linear Peptide
Arg-Met-Val-Ser-Gly-Gln-Thr-Arg-Leu-Asp-Leu-Leu-Gln-Arg Synthesis of the above peptide (P-5) can be carried out employing solid phase techniques now well known in the art. In a preferred procedure amino protected arginine, representing the —COOH terminal group of the above peptide, is coupled to a conventional solid phase peptide synthesis resin such as chloromethyl polystyrene cross-linked with 1 to 2% divinyl benzene. The amino protecting group is then selectively removed utilizing a suitable reagent whose nature will depend on the protecting group used. In the preferred embodiment the t-butyloxycarbonyl (Boc) group is utilized for amino group protection and 40% trifluoroacetic acid in methylene chloride is the selective deprotecting agent.

After deprotection, the arginine resin is treated with protected glutamine, preferably N-Boc-Glutamine, and dicyclohexylcarbodiimide in a manner known per se as to form a peptide bond between the free amino group of the arginine residue and the carboxyl group of protected glutamine.

The cycle of deprotection and coupling with amino acid derivatives and dicyclohexylcarbodiimide is then repeated with the remaining amino acids in the sequence order of the above peptide. Some of the amino acids required side-chain blocking groups besides the alpha-amino protection. Such amino acids and the blocking groups are as follows:

Met(MBzl),Ser(oBzl),Arg(Tos),Asp(oBzl),Thr(oBzl)
Where oBzl is benzyl, Tos is guanidino-p-Toluenesulfonyl and MBzl is methoxybenzyl.

Completion of the synthesis provided the following peptide coupled to the styrenedivinylbenzene copolymer resin:

TFA-Arg(Tos)-Met(mBzl)-Val-Ser(oBzl)-Gly-Gln-Thr(oBzl)-Arg(Tos)-Leu-Asp(oBzl)-Leu-Leu-Gln-Arg(Tos)-resin Decoupling of the peptide from the resin is accomplished by treatment with liquid hydrogen fluoride with concomittant cleavage of all protecting groups to produce the desired peptide.

Attachment of N-Boc-Arginine(Tos) to chloromethyl resin was performed by the cesium salt method. A sample of chloromethyl resin (200 g.) containing 0.74 mmol chloride per gram is treated with the cesium salt of Boc-Arginine(Tos) resulting from the neutralization of Boc-Arginine(Tos) with cesium carbonate. About 38.6 grams of Boc-Arginine(Tos) is dissolved in 80% methanol and 20% water and adjusted to pH 7.0 with about 29 grams of cesium carbonate. The resulting solution is dried on a rotary evaporator, then dried three more times after three additions of 100 milliliters of xylene. To the cesium salt of Boc-Arginine(Tos) was added 200 grams of chloromethyl resin as above and sufficient 1-Methyl-2-Pyrrolidinone to make about 1.90 liters total volume. The resulting mixture is stirred at 55° C. for 48 hours. The resin was then washed extensively with methanol, then water, then again with methanol. The resin was air dried, then dried under vacuum. After cleavage of Arginine from the resin with HF, amino acid analysis gave one peak corresponding to 0.48 mmol/gm.

A sample of the resin just described (6.0 g.) was submitted to the following synthesis schedule: (1) Wash with three 100 ml. portions of methylene chloride; (2) removal of the Boc group with 40% TFA in methylene chloride for a one minute wash and for a 20 minute reaction time; (3) wash with three 100 ml. portions of methylene chloride; (4) wash with two 100 ml portions of isopropanol; (5) wash with three 100 ml. portions of methylene chloride; (6) a one minute wash and ten minutes neutrallization with 100 ml. portions of 10% triethylamine in methylene chloride; (7) wash with three portions of 100 ml. of methylene chloride; (8) Add 2.5 equivalents (7.2 mmol) of Boc amino acid and 2.5 equivalents (7.2 mmol) of dicyclohexylcarbodiimide in methylene chloride and shake for 2 hours; (9) wash with three 100 ml. portions of methylene chloride; (10) wash with two 100 ml. portions of isopropanol; (11) wash with three 100 ml. portions of methylene chloride. The above cycle was repeated for the following N-protected amino acids:

| | |
|---|---|
| Boc-Gln | Boc-Thr(oBzl) |
| Boc-Leu | Boc-Gln |
| Boc-Leu | Boc-Gly |
| Boc-Asp(oBzl) | Boc-Ser(oBzl) |
| Boc-Leu | Boc-Val |
| Boc-Arg(Tos) | Boc-Met(mBzl) |
| | Boc-Arg(Tos) |

The protected peptide resin was submitted to deprotection to give the TFA salt of the protected peptide resin. The dried resin (5.88 g) was stirred in the presence of 6 ml. of anisole and 60 ml. of liquid HF at 0° C. for 1 hour. The HF was removed by vacumn and the oily residue was washed with two 50 ml. portions of ethyl ether. The peptide was extracted from the resin by three 50 ml. portions of 1 molar acetic acid and the combined filtrates were lyophilized to give 2.27 grams of crude peptide. This was purified by 250 transfers in a counter-current distribution apparatus. The solvent system for the above fractionation was butanol:acetic acid:water at 4:1:5 ratios.

Somewhat purified fractions from the counter-current distribution apparatus were further purified by column chromatography on diethylaminoethylcellulose with a linear gradient of 0.01 to 0.5 molar ammonium bicarbonate to give 250 mg. of pure peptide.

Amino acid analysis of the pure peptide after acid hydrolysis gave: ammonia 1.76, Arg 2.91, Asp 0.99, Thr 1.00, Ser 0.99, Glu 2.081, Gly 1.01, Val 1.081, Met 0.97, Leu 3.04. This peptide gave a single spot with a Rf of 0.62 on cellulose thin layer chromatography with a solvent system of butanol:pyridine:acetic acid:water of 15:10:3:12, and an Rf of 0.53 with these same solvents of 42:24:4:30.

EXAMPLE II

The respective shorter chain sequence compounds of the invention are prepared by the method of claim 1 starting with the respective C-terminal amino acids: aspartic acid for the 10-sequence compound D-1, leucine for the 11-sequence and 12-sequence compounds P-2 and P-3 and glutamine for the 13-sequence compound P-4, ending all sequences, as shown above, with the N-terminal arginine.

I claim:

1. The antigenic peptide compounds having chain lengths of from 10 to 14 amino acids arranged in a sequence from N-terminal to C-terminal amino acids which include the antigenic sequence Arg-Met-Val-Ser-Gly-Gln-Thr-Arg-Leu-Asp, said compounds being selected from the class of compounds consisting of:
    (a) Arg-Met-Val-Ser-Gly-Gln-Thr-Arg-Leu-Asp,
    (b) Arg-Met-Val-Ser-Gly-Gln-Thr-Arg-Leu-Asp-Leu,
    (c) Arg-Met-Val-Ser-Gly-Gln-Thr-Arg-Leu-Asp-Leu-Leu,
    (d) Arg-Met-Val-Ser-Gly-Gln-Thr-Arg-Leu-Asp-Leu-Leu-Gln, and
    (e) Arg-Met-Val-Ser-Gly-Gln-Thr-Arg-Leu-Asp-Leu-Leu-Gln-Arg,
wherein Gly represents glycine, and Arg, Met, Val, Ser, Gln, Thr, Leu, Asp, respectively represent the L-amino acid forms of arginine, methionine, valine, serine, glutamine, threonine, leucine, and aspartic acid.

2. The antigenic peptide of claim 1 having the amino acid sequence (a).

3. The antigenic peptide of claim 1 having the amino acid sequence (b).

4. The antigenic peptide of claim 1 having the amino acid sequence (c).

5. The antigenic peptide of claim 1 having the amino acid sequence (d).

6. The antigenic peptide of claim 1 having the amino acid sequence (e).

* * * * *

UNITED STATES PATENT AND TRADEMARK OFFICE
CERTIFICATE OF CORRECTION

PATENT NO. : 4,377,516
DATED : March 22, 1983
INVENTOR(S) : Erwin Goldberg

It is certified that error appears in the above-identified patent and that said Letters Patent are hereby corrected as shown below:

In column 1 of the patent following the title insert the following notice: -This invention was developed in part under Grant HD 05863 by The National Institutes of Health.-

Signed and Sealed this

Fifth Day of June 1984

[SEAL]

Attest:

Attesting Officer

GERALD J. MOSSINGHOFF
Commissioner of Patents and Trademarks